United States Patent [19]

Patterson

[11] 4,309,363
[45] Jan. 5, 1982

[54] NOVEL PROCESS
[75] Inventor: John A. Patterson, Fishkill, N.Y.
[73] Assignee: Texaco Inc., White Plains, N.Y.
[21] Appl. No.: 44,789
[22] Filed: May 31, 1979
[51] Int. Cl.³ ............................................ C07C 143/02
[52] U.S. Cl. .............................................. 260/513 R
[58] Field of Search .................................... 260/513 R
[56] References Cited
PUBLICATIONS
Gilbert, "Sulfonation & Related Reac.", (1965), p. 273.
Weininger, "Contemporary Org. Chem.", (1972), pp. 570–571.
Allinger, "Organic Chem.", (1972), p. 552.

*Primary Examiner*—Alan Siegel
*Attorney, Agent, or Firm*—Carl G. Ries; Robert A. Kulason; Carl G. Seutter

[57] ABSTRACT

Metal isethionates are carboxylated to metal isethionate carboxylates which are pyrolyzed to metal vinyl sulfonates.

13 Claims, No Drawings

NOVEL PROCESS

FIELD OF THE INVENTION

This invention relates to a process for preparing metal vinyl sulfonates.

BACKGROUND OF THE INVENTION

As is well known to those skilled in the art, sulfoethoxylation may be effected by use of compounds such as sodium isethionate (also called hydroxyethane sodium sulfonate-HESS) or sodium vinyl sulfonate (SVS). It has been found that the latter compound is more reactive under certain conditions than is the former; and accordingly it may be desirable to covert the former to the latter to attain the benefits inherent in the greater reactivity.

It is an object of this invention to provide a process for preparing metal vinyl sulfonates. Other objects will be apparent to those skilled in the art.

STATEMENT OF THE INVENTION

In accordance with certain of its aspects, the novel process of this invention may comprise adding a metal isethionate carboxylate to a pyrolysis zone; maintaining said pyrolysis zone containing said metal isethionate carboxylate at pyrolyzing conditions during a decomposition period thereby forming product metal vinyl sulfonate and carboxylic acid; and recovering said product metal vinyl sulfonate from said pyrolysis zone.

DESCRIPTION OF THE INVENTION

Charge material which may be used in practice of the process of this invention is preferably an alkali metal isethionate. The preferred charge material is sodium isethionate $HOCH_2CH_2SO_3Na$.

This preferred charge material may be available or it may be prepared preferably by the reaction of substantially equimolar quantities of ethylene oxide and sodium bisulfite (in aqueous solution) at 20° C.-200° C. over 1-25 hours. Product may be recovered by cooling the solution to 0° C.-25° C. and filtering. The product may preferably be dried under vacuum of 10-500 mm Hg for 1-24 hours.

Commercially available (preferably anhydrous) sodium isethionate may be used as charge material.

Acylation of the metal isethionate may be carried out by reaction of preferably equivalent quantities of the preferred sodium isethionate and the preferred acetic anhydride. Reaction is in liquid phase at temperature which may be as low as room temperature, but more preferably is elevated to at least about 50° C. It is preferred that reaction be carried out at reflux. Reaction temperature may be 20° C.-150° C., preferably 50° C.-150° C., say 130° C.

Acylation may be carried out by use of an anhydride of an organic carboxylic acid, preferably an alkyl carboxylic acid such as acetic anhydride, propanoic anhydride, butanoic anhydride etc. Other acylating agents which may be employed may include acid halides such as acid chlorides including acetyl chloride and acid bromides such as acetyl bromide.

In the preferred embodiment, acetylation is carried out with acetic anhydride.

Reaction is preferably carried out in the presence of a diluent-solvent which may be any liquid which is essentially inert under the conditions of reaction i.e. which either does not react with the reactants or products or which reacts to produce innocuous materials which do not interfere with the reaction. A preferred inert diluent-solvent may be the acid corresponding to the acylating agent.

Thus in one embodiment, substantially equivalent proportions of the preferred sodium isethionate may be reacted with the preferred acetic anhydride in the presence of an excess of diluent-solvent anhydrous (i.e. glacial) acetic acid. Typically the acetic anhydride may be added dropwise to the mixture of sodium isothionate and acetic acid while the temperature is maintained at room temperature to say 40° C., typically 30° C.

After addition of the acetic anhydride is complete, the reaction mixture is heated to 150° C.-300° C., preferably to reflux temperature of 120° C.-150° C., say 132° C. for 0.5-3 hours, say one hour.

The reaction mixture is then cooled to 20° C.-40° C., say room temperature of 20° C. at which point it may normally solidify. The solid mixture is preferably slurried with 10-200 times its weight of low-boiling liquid, such as acetone, diethyl ether, dipropyl ether, benzene, etc. preferably acetone. The slurry is filtered and the washed solid filter cake contains typically sodium isethionate acetate (in yield of 50%-100%) say 75% based upon charge sodium isethionate. Typically the acetate is a solid crystalline material. The product may contain some acetic acid which need not be removed prior to the subsequent steps.

The composition so prepared, which commonly contains 75%-90% by weight of sodium isethionate acetate plus 10%-25% by weight of acetic acid may be purified by further washing with 1-5 times its weight of an ether, preferably ethyl ether followed by washing with 1-5 times its weight of petroleum ether. The product, after filtering and drying typically is obtained in 60%-95%, say 90% yield based upon starting sodium isethionate. It has a purity of 80%-99%, say 99%.

It is possible to convert the sodium isethionate carboxylate to desired sodium vinyl sulfonate by pyrolyzing the sodium isethionate carboxylate in a pyrolysis zone. Although it may be possible to pyrolyze this material neat—with no added compositions—it is preferred that it be carried out in the presence of an inert high-boiling liquid. Preferred high-boiling liquids may be hydrocarbons, high-boiling ethers, etc. One illustrative type of material is alkoxylated phenols, such as ethoxylated nonyphenols. A preferred composition is the ethoxylated nonylphenol marketed under the trademark Surfonic N-40. Other preferred compositions may include kerosene, triethylene glycol, ethoxylated dodecylphenol, butyl carbitol, $C_{12}$-$C_{20}$ n-paraffins, etc.

It is preferred that the high-boiling liquids used in the pyrolysis reaction possess a boiling point above about 150° C., preferably about 200° C.-350° C. Typically these liquids may be liquid at ambient temperature and have a boiling point (or boiling range) up to 350° C., preferably 300° C.

As the mixture of preferably sodium isethionate acetate and Surfonic N-40 brand of nonylphenol ethoxylate is heated to 150° C.-300° C., preferably 200° C.-250° C., preferably 200° C. over 1-20 hours, say 6 hours at 0.2-760 mm Hg, say 760 mm Hg, the liquid is preferably purged with a slow stream of inert gas such as nitrogen.

At the end of the reaction, the mixture is cooled to room temperature. Solid product contains 1%-20%, say 10.3% of unreacted sodium isethionate acetate, 10%-50%, say 27.5% sodium vinyl sulfonate and 5%–75%, say 62.2% sodium isethionate in the excess of the high boiling liquid. Acetic acid and other light ends are recovered in the gas stream. The solid is separated from the high boiling liquid.

The product mixture of sodium isethionate acetate, sodium vinyl sulfonate, and sodium isethionate may be used as sulfoethylating agent as so recovered.

It is found that the product sodium vinyl sulfonate, whether pure or impure form may be used as sulfoethylating agents for alcohols, mercaptans, ethoxylates etc.

DESCRIPTION OF PREFERRED EMBODIMENTS

Practice of the process of this invention may be observed from the following illustrative examples wherein as elsewhere in the specification, all parts, percentages, etc. are by weight unless otherwise noted.

EXAMPLE I

2 HOCH$_2$CH$_2$SO$_3$Na + (CH$_3$CO)$_2$O

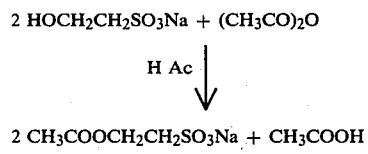

2 CH$_3$COOCH$_2$CH$_2$SO$_3$Na + CH$_3$COOH

In this example, sodium isethionate acetate is prepared by the reaction of sodium isethionate and acetic anhydride. Commercially available (purity above 95%) sodium isethionate (29.0 parts, 0.2 moles) is added to 24 parts of anhydrous glacial acetic acid solvent. Acetic anhydride (20.5 parts, 0.201 moles) is then added dropwise as the temperature is maintained at 30° C. After addition of the acetic anhydride, the mixture is refluxed (ca 132° C.) for one hour; and it is then cooled to room temperature.

Upon cooling, the reaction mixture solidifies. It is slurried in 100 parts by volume of acetone and filtered. The washed filter cake is found to be sodium isethionate acetate attained in approximately quantitative yield.

EXAMPLE II

In this example, the procedure of Example I is followed except that (i) the reaction mixture also contains 0.05 parts anhydrous zinc chloride;

(ii) the acetic anhydride is added dropwise over 25 minutes;

(iii) reflux temperature is 130° C.;

(iv) the acetic acid is evaporated using a rotary evaporator under vacuum.

The product (28.77 parts) is found, by NMR, to be sodium isethionate acetate. Yield is 75.7% based on charge sodium isethionate.

EXAMPLE III

The products of Examples I and II are mixed and slurried with 150 parts by volume diethyl ether and filtered. The filter cake is then slurried in 150 parts by volume of petroleum ether, filtered, and dried. Product is purified sodium isethionate acetate (analyzed by NMR) in amount of 70.63 parts. Purity was greater than 90%.

A mixture of 19 parts of the purified sodium isethionate acetate so obtained and 34.9 parts of the Surfonic N-40 brand of ethoxylated nonyl phenol (m. wt. ca 396 and containing 4 ethoxy groups per nonyl phenol moiety) and 0.56 parts of anhydrous potassium hydroxide is heated to 200° C.–202° C. over 6 hours while being purged with a slow stream of nitrogen. The mixture is then cooled and filtered.

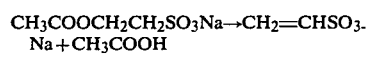

The solid product (13.74 parts) contains 10.3% recovered sodium isethionate acetate, 27.5% sodium vinyl sulfonate, and 62.2% sodium isethionate. The filtrate (22.68 parts) is principally the ethoxylated nonylphenol. Acetic acid and light ends are removed in the gas stream.

Sodium vinyl sulfonate is separated from the solid by fractional crystallization.

Comparable results may be obtained if the sodium isethionate is replaced by:

| Example | Component |
|---------|-----------|
| IV | HOCH$_2$CH$_2$SO$_3$K |
| V | HOCH CH$_2$SO$_3$K<br>\|<br>CH$_3$ |
| VI | HOCHCH$_2$SO$_3$Na<br>\|<br>CH$_3$ |

Comparable results may be obtained if the high-boiling inert-solvent is:

| Example | Diluent-Solvent |
|---------|-----------------|
| VII | kerosene |
| VIII | triethylene glycol |

Although this invention has been illustrated by reference to specific embodiments, it will be apparent to those skilled in the art that various changes and modifications may be made which clearly fall within the scope of this invention.

I claim:

1. The method which comprises
adding a metal isethionate carboxylate to a pyrolysis zone;
maintaining said pyrolysis zone containing said metal isethionate carboxylate at pyrolyzing conditions including temperature of 150° C.–300° C. during a decomposition period thereby forming product metal vinyl sulfonate and carboxylic acid; and
recovering said product metal vinyl sulfonate from said pyrolysis zone.

2. The method claimed in claim 1 wherein said metal is an alkali metal.

3. The method claimed in claim 1 wherein said metal is sodium and said metal isethionate carboxylate is metal isethionate acetate.

4. The method claimed in claim 1 wherein said pyrolyzing conditions include time of 2–15 hours.

5. The method which comprises
adding sodium isethionate acetate to a pyrolysis zone;
maintaining said pyrolysis zone containing said sodium isethionate acetate at pyrolyzing conditions, including temperature of 150° C.–300° C., during a decomposition period thereby forming product sodium vinyl sulfonate and acetic acid; and
recovering said product sodium vinyl sulfonate from said pyrolysis zone.

6. The method which comprises adding sodium isethionate acetate to a pyrolysis zone together with an inert high-boiling liquid;

maintaining said sodium isethionate acetate and said inert high-boiling liquid in said pyrolysis zone at pyrolizing conditions including temperature of 150° C.–300° C. during a decomposition period thereby forming product sodium vinyl sulfonate and acetic acid; and recovering said product sodium vinyl sulfonate from said pyrolysis zone.

7. The method as claimed in claim 6 wherein said inert high-boiling liquid is an alkoxylated phenol.

8. The method as claimed in claim 6 wherein said inert high-boiling liquid is ethoxylated nonyl phenol.

9. The method as claimed in claim 6 wherein said inert high-boiling liquid is a $C_{12}$–$C_{20}$ n-paraffin.

10. The method as claimed in claim 6 wherein said inert high-boiling liquid in said pyrolizing conditions include temperature of 150° C.–300° C. and decomposition period of 1–20 hours.

11. The method which comprises adding sodium isethionate acetate to a pyrolysis zone together with ethoxylated nonyl phenol liquid;

maintaining said pyrolysis zone at pyrolyzing conditions including temperature of 150° C.–300° C. during decomposition period of 1–20 hours thereby forming product sodium vinyl sulfonate; and recovering said product sodium vinyl sulfonate from said pyrolysis zone.

12. The method which comprises adding a metal isethionate and acylating agent to a reaction mixture;

maintaining said reaction mixture in liquid phase during a reaction period thereby forming product metal isethionate carboxylate;

pyrolyzing said metal isethionate carboxylate in a pyrolysis zone at pyrolyzing conditions including temperature of 150° C.–300° C. during a decomposition period thereby forming product metal vinyl sulfonate and carboxylic acid; and recovering said product metal vinyl sulfonate from said pyrolysis zone.

13. The method claimed in claim 12 wherein said metal is an alkali metal.

* * * * *